United States Patent [19]

Fox, Jr. et al.

[11] Patent Number: 4,612,337
[45] Date of Patent: Sep. 16, 1986

[54] METHOD FOR PREPARING INFECTION-RESISTANT MATERIALS

[75] Inventors: Charles L. Fox, Jr., Fort Lauderdale, Fla.; Shanta M. Modak, River Edge, N.J.

[73] Assignee: The Trustees of Columbia University in the City of New York, New York, N.Y.

[21] Appl. No.: 739,424

[22] Filed: May 30, 1985

[51] Int. Cl.$^4$ .......................................... A61K 31/625
[52] U.S. Cl. ..................... 523/113; 424/27; 128/127; 128/335.5; 435/1; 523/115; 604/265; 604/285; 8/94.11
[58] Field of Search ................. 523/113, 115; 8/94.11; 424/27; 128/127, 335.5; 435/1; 604/265, 285

[56] References Cited

U.S. PATENT DOCUMENTS

| | | | |
|---|---|---|---|
| 4,049,802 | 9/1977 | Fox | 424/27 |
| 4,271,070 | 6/1981 | Miyata et al. | 424/27 |
| 4,353,996 | 10/1982 | Marconi et al. | 424/27 |
| 4,401,712 | 8/1983 | Morrison | 424/27 |
| 4,404,197 | 9/1983 | Fox et al. | 424/27 |
| 4,446,124 | 5/1984 | Fox et al. | 424/27 |
| 4,455,146 | 6/1984 | Noda et al. | 424/27 |
| 4,462,981 | 7/1984 | Smith | 424/27 |
| 4,563,485 | 1/1986 | Fox et al. | 424/27 |
| 4,563,489 | 1/1986 | Urist | 523/115 |

OTHER PUBLICATIONS

"Vascular Prosthetic Infection", Bennion et al., Infections in Surgery, Sep. 1982, pp. 45–55.
"Control of Burn Wound Infections by Pefloxacin and its Silver Derivative", Modak et al., Burns, 10, No. 3, pp. 170–178.
"Topical Therapy and the Development of Silver Sulfadiazine", Fox, Jr., Surgery, Gyn & Ob, 157, 82–88, Jul. 1983.
"Virulence of Pseudomonas Infection in Burned Rats and Mice", Fox et al., Arch Surg., 101, pp. 508–512, Oct. 1970.
"Crystal Structure of 2-Sulfanilamidopyrimidinesilver(1)", Baenziger, et al., Inorganic Chemistry, 15, No. 8, pp. 1807–1809, (1976).
"Silver Treated Graft Materials for Coverage of Infected Burn Wounds", Fox et al., Ann. Chir. Plast., 1979, 24, No. 3, pp. 265–267.
"Sulfadiazine Silver-Resistant Pseudomonas in Burns", Modak et al., Arch Surg., 116, 854–857, Jul. 1981.
"Antibiotic Bonding to Polytetrafluoroethylene with Tridodecylmethylammonium Chloride", Harvey et al., Surgery, Sep. 1982, pp. 504–512.

*Primary Examiner*—Ronald W. Griffin
*Attorney, Agent, or Firm*—Brumbaugh, Graves, Donohue & Raymond

[57] ABSTRACT

An infection-resistant polymeric material, such as polytetrafluoroethylene, for use on or within a human or animal body, for example, in the form of a vascular graft, can be prepared by an improved method which comprises the following sequence of steps: (a) soaking a polymeric material with a solution of an antimicrobial agent, such as sodium sulfadiazine, oxacillin dissolved in an organic solvent therefor, such as an ethanol/chloroform mixture, (b) soaking the polymeric material with an organic solvent, such as ethanol, for a metal salt; and (c) resoaking the polymeric material with the solution of the antimicrobial agent dissolved in the organic solvent therefor. The polymeric material is dried after each soaking step. Preferably, in the intermediate soaking step (b) the organic solvent contains a metal salt, such as silver nitrate, dissolved therein, so as to form in situ the metal salt of the antimicrobial agent, such as silver sulfadiazine.

15 Claims, No Drawings

METHOD FOR PREPARING INFECTION-RESISTANT MATERIALS

BACKGROUND OF THE INVENTION

The present invention relates to the preparation of infection-resistant materials for use on or within a human or animal body and more particularly to an improved method of preparing infection-resistant materials wherein antimicrobial agents, and preferably metal salts of anti-microbial agents, are incorporated directly into various polymeric materials, including hydrophobic polymeric materials.

Infection is a common complication occasioned from any injury, surgical procedure, or introduction of foreign material, such as a prosthetic device, into a human or animal body. Various techniques and means for alleviating infection, such as topical application of antibiotics, systemic administration of antibiotics, and maintenance of sterility of the operating surroundings, instruments, bandages, etc., are in common use. However, these techniques have not been particularly effective in preventing infection associated with in-dwelling, or surgically implanted, devices intended to remain in the body, or in direct contact with the body, for an extended period of time.

Prior U.S. patent application for Ser. Nos. 605,792 and 605,793, filed on Apr. 30, 1984 and assigned to the assignee hereof, now U.S. Pat. No. 4,563,485, issued Jan. 7, 1986 and U.S. Pat. No. 4,581,028, issued Apr. 8, 1986 respectively, discuss at length the problems associated with in-dwelling and surgically implanted devices wherein long-term infection preventive ability is desired. The aforementioned applications for letters patent are hereby cross-referenced and their entire disclosures are incorporated herein by reference. Briefly, the referenced patent applications are directed to the incorporation of metal salts of sulfonamides or nalidixic acid derivatives and metal salts of nalidixic acid derivatives into natural or synthetic polymeric materials by treating the polymeric materials with an aqueous solution or suspension of the antimicrobial agent. In order to provide adequate absorption or adherence of the antimicrobial agent within the polymeric materials, they are preliminarily treated or coated with gelatin or albumin or a surfactant, such as tridodecylmethyl ammonium chloride. The materials created by the incorporation of the above-referenced antimicrobial agents are ideally suited for body-invasive uses such as vascular grafts, heart valves, bone and joint replacements, etc.

Prevention of infection in vascular reconstructive surgery, in particular, has been the subject of much study in view of the high mortality rate, or catastrophic effects, should infection occur. Typically, systemic antibiotics are administered and the graft site is locally irrigated with an antibiotic solution. The graft is also soaked in an aqueous solution of an antibiotic immediately prior to implantation. However, these techniques have not proven to be completely effective due to the brief residence of antibacterial agents at the implantation site. Moreover, due to the ineffectiveness of known techniques, use of prosthetic grafts in contaminated wounds of trauma victims is interdicted due to lack of anti-bacterial action at the graft site. Incorporation of antibiotics in the graft material, as discussed above, would yield a higher concentration of antibiotic agent at the graft site and would permit slow release of the agent to provide a prolonged concentration of antibiotic at the graft site.

The common practice in the prior art is to bond the antibiotic to a coating on, for example, Dacron polyester or polytetrafluoroethylene (Teflon) graft materials. Known coatings include gelatin, albumin, graphite-benzalkonium chloride and cationic surfactants such as tridodecylmethylammonium chloride (TDMAC). In fact, it was heretofore believed that it was necessary to coat the hydrophobic materials (e.g., PTFE) in order to bond an antibacterial agent thereto.

The coatings, such as TDMAC, present a cationic surface which bonds the anionic antibiotic. The antibiotic is, nevertheless, rapidly dissipated in the body fluids. A certain amount of antibiotic, however, does remain in the coating until the coating dissipates from the substrate material. Adverse effects, such as toxicity and thrombogenesis, are possible. In particular, the cationic coating which is present after the anionic antibiotic has been absorbed into the body may be thrombogenic. A further disadvantage of the coated grafts is that they are inconvenient to use. The manufacturers of such grafts provide them with the coating, but not with the antibiotic. Thus, the grafts must be soaked in an aqueous antibiotic solution at the operating table.

SUMMARY OF THE INVENTION

It is therefore the principle object of the present invention to provide an improved method for incorporating significant amounts of antimicrobial agents into polymeric materials without the necessity of preliminarily coating the polymeric materials with a carrier or a surfactant and for obtaining products having long-lasting antimicrobial effects and biphasic release of the antimicrobial agents.

In accordance with the present invention, there is provided a method for preparing an infection-resistant polymeric material for use on or within a human or animal body which comprises the following sequence of steps:

(a) soaking a polymeric material with a solution of an antimicrobial agent dissolved in an organic solvent therefor, (b) soaking the polymeric material with an organic solvent for a metal salt, (c) resoaking the polymeric material with the solution of the antimicrobial agent dissolved in the organic solvent therefor, and (d) drying the polymeric material after each soaking step.

Preferably, in the intermediate soaking step (b) the organic solvent contains a metal salt dissolved therein.

The intermediate soaking step (b) of the method of the present invention is particularly important. Thus, it was found that the amount of antimicrobial agent which could be incorporated into the polymeric material could not be increased merely by repeatedly or successively soaking the polymeric material with the solution of the antimicrobial agent dissolved in the organic solvent. On the other hand, it was found quite unexpectedly that the amount of antimicrobial agent which can be incorporated into the polymeric material can be appreciably increased by means of the intermediate soaking step (b). It is believed that the intermediate soaking step (b) activates the surface of the previously soaked polymeric material so that it is then receptive to the incorporation of additional antimicrobial agent by resoaking the polymeric material with the solution of the antimicrobial agent dissolved in the organic solvent. Moreover, the intermediate soaking step (b) serves as a means of converting in situ the antimicrobial agent soaked into the polymeric material into a metal salt thereof, such as a silver salt thereof, which has longer lasting antimicrobial activity and biphasic release characteristics, i.e., the antimicrobial agent is released from the polymeric material rapidly at first and then followed by a slow, steady release over a prolonged period.

DETAILED DESCRIPTION OF THE INVENTION

In the above-described method of the present invention, the polymeric materials can be natural polymeric materials or synthetic polymeric materials, including homopolymers and copolymers. Examples of suitable polymeric materials include polyamide, polyester, polyethylene, polypropylene, polystyrene, polytetrafluoroethylene, polyurethane, polyvinylchloride, cellulose acetate, silicone elastomers, collagen, silk, etc.

The polymeric materials can be knit or woven fabrics, single or plural filaments, laminates, extruded or molded items, etc., useable on or within a human or animal body, such as wound dressings, vascular grafts, catheters, sutures, skin buttons, synthetic heart valves, feminine hygiene products, cannulas, pacemakers, etc.

Any antimicrobial agent which is compatible with a human or animal body can be used in the method of the present invention. Representative antimicrobial agents include norfloxacin, oxacillin, nafcillin, sulfadiazine, pefloxacin, tobramycin, piromidic acid, pipemidic acid, enoxacin, AM-833, and cephalosporins, such as cefmenoxime, moxalactam, cefazolin, cefamandole, etc.

Any organic solvent which solubilizes the antimicrobial agent can be used in the soaking and resoaking of the polymeric material with the antimicrobial agent solution. Typical suitable organic solvents include acetic acid, chloroform, ethanol, acetone, ether, etc.

The organic solvent used in the intermediate soaking step (b) is one capable of solubilizing the metal salt. Ethanol is typical of such useable organic solvents.

Metal salts useable in the intermediate soaking step (b) in the preferred embodiment of the invention include silver nitrate, zinc nitrate, cerium chloride, and the like. As noted above, these metal salts, react with the antimicrobial agent in the soaked polymeric material to provide in situ metal-mediated antimicrobial agents having long-lasting antimicrobial activity in the infection-resistant polymeric material products obtained by the method of the present invention, which products have the property of biphasic release of the antimicrobial agent therefrom.

Concentrations of the soaking solutions, soaking times, drying techniques and drying periods are not important features of the method of the present invention. Representative examples of such operating conditions are set forth in the Examples and Experiments hereinafter which are illustrative of the improved method of the present invention and the results obtained thereby.

EXAMPLE 1

A polytetrafluoroethylene (PTFE) vascular graft (Gore-Tex) supplied by W.L. Gore and Associates, Inc., Maryland, was rendered infection-resistant by the following method: A 10 cm segment of a 5 mm diameter graft was soaked in a first solution containing 30 mM of norfloxacin for 5 minutes. The norfloxacin solution was prepared by dissolving the norfloxacin in acetic acid and then diluting the acetic acid with chloroform to a 1:25 proportional mixture by volume. The norfloxacin-treated graft was then air dried. After drying, the graft was soaked in a second 25 mM ethanolic solution of silver nitrate for 5 minutes. The graft was air dried, preferably in the dark, and was resoaked in the first norfloxacin-containing solution for another 5 minutes. The graft was again air dried to remove all traces of solvent, washed with distilled, deionized water to remove unbound norfloxacin from the surface, and dried in a vacuum desiccator. The end result was a PTFE vascular graft into which silver norfloxacin was incorporated.

The above procedure was repeated, but oxacillin, nafcillin and pefloxacin were separately substituted for the norfloxacin to provide PTFE grafts into which the silver salts of these three other antimicrobial agents were incorporated.

The treated grafts were stored in the dark in a refrigerator until ready for use. Prior to in vivo use, the grafts may be sterilized with ethylene oxide in a manner well known to those of skill in the art.

EXAMPLE 2

The procedure of Example 1 was followed using separately norfloxacin, oxacillin, nafcillin, pefloxacin and tobramycin as the antimicrobial agent, but with the exception that the second or intermediate soaking solution was ethanol alone (i.e., there was no silver nitrate dissolved therein). The end result was in each case a PTFE vascular graft into which only the antimicrobial agent, rather than the silver salt thereof, was incorporated.

All solutions in the above described Examples 1 and 2 were at room temperature (37° C.). As pointed out previously, temperature and time of soaking are not critical, and can be modified for different organic solvent systems by those skilled in the art. Moreover, it should be noted that the molar concentrations of antimicrobial agent and metal salt are given for the purpose of illustration, and can also be varied by those skilled in the art, because they are greatly in excess of the therapeutically effective amount. It is the ability to incorporate such a high concentration of antimicrobial agent at the potential site of infection that is a significant advantage of the present invention over the prior art.

EXAMPLE 3

A PTFE vascular graft of the same type as in Example 1 was incorporated with silver sulfadiazine by the following technique: A 10 cm segment of the graft was soaked in a 30 mM solution of sodium sulfadiazine at 37° C. for 5 minutes. The sodium sulfadiazine solution was prepared by dissolving the sodium sulfadiazine in a minimal amount of water, and then mixing in a mixture of ethanol and chloroform in a 4:1 proportional mixture by volume. The sulfadiazine-treated graft was air dried and soaked in a 25 mM ethanolic solution of silver nitrate for 5 minutes at 37° C.

The graft was air dried, resoaked in the sodium sulfadiazine solution, air dried, washed, redried, and stored in the same manner as described above in Example 1. The end result was a PTFE vascular graft into which silver sulfadiazine was incorporated.

EXAMPLE 4

In another embodiment, in the second or intermediate soaking step of Example 3 the ethanol did not contain silver nitrate. The end result was a PTFE vascular graft into which only the sulfadiazine, rather than the silver salt thereof, was incorporated.

EXAMPLE 5

A Dacron polyester vascular graft supplied by C.R. Bard, Inc., Implants Division, Billerica, MA, was incorporated with either silver norfloxacin or with oxacillin in accordance with the techniques set forth in Examples 1 or 2, respectively.

EXAMPLE 6

The procedure for bonding an antibiotic to Dacron polyester grafts is similar to that described for PTFE grafts. However, a slight modification of the procedure did improve the efficacy of the graft. Unlike PTFE grafts, Dacron polyester grafts tend to bleed through the small apertures between the knitted or woven threads. This can be reduced, if the graft is prepared by the modified method which is as follows. The graft is soaked in the first antibiotic solution and then soaked in the intermediate ethanolic solution. The third soaking is done in the original antibiotic solution containing a small amount of polylactic acid, e.g., 5% by weight. This permits formation of an antibiotic film around the graft.

EXPERIMENTAL RESULTS (A) The efficacy of bonding norfloxacin and oxacillin and the silver salts thereof to a PTFE vascular graft by prior art techniques, and by the procedure of the present invention, is shown below in Table I by the concentration of the antimicrobial agent incorporated on the PTFE sample and the antimicrobial activity of the sample in a blood culture.

PTFE vascular graft samples were prepared by the bonding procedures of Examples 1 and 2 hereinabove. In the Table I, "DIRECT" means that the sample was treated by the procedure of Example 2 and "DIRECT+SILVER" means that the sample was treated by the procedure of Example 1.

For purposes of comparison, tridodecylmethyl ammonium chloride (TDMAC) coated PTFE samples were prepared by soaking segments of PTFE vascular grafts in a 5% ethanolic solution of TDMAC for 1 hour at room temperature. The TDMAC-treated grafts were air dried for about 5 minutes and then soaked in an aqueous solution of the referenced antimicrobial agent. "TDMAC+SILVER" indicates that the antimicrobial-treated TDMAC samples were further soaked in an aqueous solution of silver nitrate.

For further purposes of comparison, PTFE graft specimens were incorporated with "Silver Alone" by soaking a PTFE sample or a TDMAC-coated PTFE sample in an ethanolic solution of silver nitrate.

TABLE I

| Graft Bonded With: | Bonding Procedure | Drug Concentration ($\mu$ mole/2 cm) | Antibacterial Activity (colony count) |
|---|---|---|---|
| None (Control) | — | — | $2 \times 10^8$ |
| Norfloxacin | TDMAC | 4.0 | 0 |
| Norfloxacin | DIRECT | 5.0 | 0 |
| Norfloxacin | TDMAC + SILVER | 4.0 | 0 |
| Norfloxacin | DIRECT + SILVER | 7.2 | 0 |
| Oxacillin | TDMAC | 5.0 | 0 |
| Oxacillin | DIRECT | 4.0 | 0 |
| Oxacillin | TDMAC + SILVER | 5.0 | 0 |
| Oxacillin | DIRECT + SILVER | 5.5 | 0 |
| Silver Alone | TDMAC | 3.5 | $1 \times 10^8$ |
| Silver Alone | DIRECT | 4.0 | $1 \times 10^8$ |

The drug in the graft was extracted for the measurement by soaking in 1:1 proportional mixture of ethanol and normal saline containing 10 mM sodium hydroxide. The drug concentration on 2 cm segments of the treated PTFE graft specimens was measured spectrophotometrically at wavelengths of 273 nm for norfloxacin and 195 nm for oxacillin. The concentrations of antimicrobial agent, shown in Table I, are not absolute due to the method of measurement, but the relative uptake of the antimicrobial agents onto the graft is still shown.

To measure the antimicrobial activity of the treated PTFE graft specimens, under simulated in vivo conditions, a 2 cm segment of each specimen was soaked for 24 to 48 hours in 5 ml of human blood which was innoculated with $10^7$ Staphalococcus aureus organisms (a clinical isolate from the Columbia-Presbyterian Hospital in New York City which is coagulase positive and penicillin resistant). Due to the interference of blood, at the appropriate wavelengths, the spectrophotometric concentration of the antimicrobial agent, after soaking, could not be measured. The antibacterial activity of the graft segments was measured by spreading aliquots of the human blood culture on blood agar plates and performing a colony count after a 24 hour incubation.

Table I shows that the DIRECT bonding technique caused the graft segment to bind a higher concentration of norfloxacin than the TDMAC technique. A higher concentration of oxacillin, on the other hand, was bound by the TDMAC method than by the DIRECT bonding technique. The highest concentration of bonded norfloxacin and oxacillin, however, was produced by the silver-mediated bonding (DIRECT+SILVER) wherein the silver-antimicrobial agent was formed in situ. It is interesting to note that the amount of antimicrobial agent bonded to the TDMAC-coated grafts was not increased by the silver-mediated bonding (TDMAC versus TDMAC+SILVER).

It is also significant to note that other experiments showed that repeated or successive soaking of the graft specimens with a higher antimicrobial agent concentration or with longer soaking times, while omitting the intermediate step of soaking the graft specimens with an organic solvent, did not increase the amount of antimicrobial agent uptake. However, the step of repeating the soaking in the first antimicrobial agent-containing solution, after intermediate soaking in the organic solvent (with or without a metal salt dissolved therein) did cause an increase in the amount of antimicrobial agent bound to the graft. This shows the importance of the intermediate soaking step which is believed to activate the surface of the graft specimen so as to accept more antimicrobial agent.

(B) Since the silver-mediated bonding increased the uptake of antimicrobial agent, the effects of other metals were investigated and the results are shown below in Table II.

Uncoated PTFE vascular graft specimens were prepared according to the procedures of Examples 1 and 3 with norfloxacin, oxacillin, nafcillin and sulfadiazine, respectively, as the antimicrobial agent in the first soaking solution. For comparative purposes, silver nitrate, bivalent zinc nitrate, and trivalent cerium chloride were used as the metal salts in the second or intermediate soaking solution. In Table II "None" indicates that the second or intermediate soaking solution contained only ethanol and no metal salt per procedure of Examples 2 and 4.

TABLE II

| Graft Bonded With | Metal used in Bonding | Drug Concentration ($\mu$ mole/2 cm) | Antibacterial Activity (colony count) | |
|---|---|---|---|---|
| | | | $10^4$ | $10^7$ |
| Norfloxacin | None | 5.0 | 0 | 0 |
| Norfloxacin | Silver | 7.2 | 0 | 0 |
| Norfloxacin | Zinc | 10.0 | 0 | 0 |
| Norfloxacin | Cerium | 13.0 | 0 | 0 |
| Oxacillin | None | 4.0 | 0 | 0 |
| Oxacillin | Silver | 5.5 | 0 | 0 |
| Oxacillin | Zinc | 5.0 | 0 | 0 |
| Oxacillin | Cerium | 5.5 | 0 | 0 |
| Nafcillin | None | 3.9 | 0 | 0 |
| Nafcillin | Silver | 6.3 | 0 | 0 |
| Nafcillin | Zinc | 4.6 | 0 | 0 |
| Nafcillin | Cerium | 5.3 | 0 | 0 |
| Sulfadiazine | None | 2.1 | 0 | $1 \times 10^6$ |
| Sulfadiazine | Silver | 6.0 | 0 | $1 \times 10^6$ |
| Sulfadiazine | Zinc | 6.3 | 0 | $1 \times 10^6$ |
| Sulfadiazine | Cerium | 5.9 | 0 | $1 \times 10^6$ |

Radioactive silver ($^{110}$AgNO$_3$), zinc ($^{65}$Zn(NO$_3$)$_2$), and cerium ($^{144}$CeCl$_3$) were used in the bonding procedure. The antimicrobial agent in a 2 cm segment of each PTFE graft specimen was extracted in a 1:1 proportional mixture of ethanol and normal saline containing 10mM sodium hydroxide. The concentration of the antimicrobial agents—norfloxacin, oxacillin, nafcillin and sulfadiazine—were measured spectrophotometrically at wavelengths of 273 nm, 195 nm, 239 nm and 260 nm, respectively. As discussed above, the concentration of antimicrobial agent in the bloodsoaked graft specimens could not be measured spectrophotometrically.

The antibacterial activity, under simulated in vivo conditions, was determined by the same procedure as described above in connection with the experiment of Table I. In this particular experiment, antibacterial activity was tested in human blood cultures which were inoculated with $10^4$ and $10^7$ organisms, respectively, of *Staph. aureus*.

The data in Table II, like that in Table I, show that the metal-mediated bonding of the antimicrobial agents to the PTFE graft specimen increased the drug concentration therein. Reference to Table II also shows that there may be a relationship between the amount of norfloxacin bound and the valence state of the metal; the trivalent cerium binding the highest amount of norfloxacin. However, in the cases of the other antimicrobial agents tested, the amount of antimicrobial agent bound did not vary significantly with the metal used. This could be due to the fact that, unlike the metal salts of norfloxacin, the zinc and cerium salts of oxacillin, nafcillin and sulfadiazine, are more soluble in the organic solvents used in the bonding procedure, and therefore, may have been diffused out of the PTFE graft specimen during the bonding procedure.

(C) The relative stability of the various antimicrobial agent and metal-antimicrobial agent complexes, bonded to the PTFE vascular graft specimens prepared in connection with the experiment of Table II, in the presence of (1) normal saline and (2) blood, was determined. The results are shown on Table III. Segments of the treated PTFE graft specimen (2 cm in length) were irrigated by forcing 40 ml of normal saline, or 40 ml of human blood, through the graft segment with a syringe. The antimicrobial agent concentration levels and antibacterial activity were measured by the same techniques described above in connection with Table I. The sulfadiazine grafts were active only against $10^4$ *Staph. aureus*, whereas all of the other grafts were active against $10^7$ *Staph. aureus*.

TABLE III

| Graft Bonded With: | Metal Used in Bonding | Antibiotic Concentration (see Table II) | Saline Irrigation | | Blood Irrigation |
|---|---|---|---|---|---|
| | | | Antibiotic Concentration ($\mu$ mole 2 cm) | Antibacterial Activity (Colony Count in Culture) | Antibacterial Activity (Colony Count in Culture) |
| Norfloxacin | None | 5.0 | 3.0 | 0 | 0 |
| Norfloxacin | Silver | 7.2 | 5.0 | 0 | 0 |
| Norfloxacin | Zinc | 10.0 | 5.0 | 0 | 0 |
| Norfloxacin | Cerium | 13.0 | 5.5 | 0 | 0 |
| Oxacillin | None | 4.0 | 2.0 | 0 | 0 |
| Oxacillin | Silver | 5.5 | 3.2 | 0 | 0 |
| Oxacillin | Zinc | 5.0 | 2.0 | 0 | 0 |
| Oxacillin | Cerium | 5.5 | 2.2 | 0 | 0 |
| Nafcillin | None | 3.9 | 2.8 | 0 | 0 |
| Nafcillin | Silver | 6.3 | 5.0 | 0 | 0 |
| Nafcillin | Zinc | 4.6 | 3.0 | 0 | 0 |
| Nafcillin | Cerium | 5.3 | 3.3 | 0 | 0 |
| Sulfadiazine | None | 2.1 | 1.7 | 0 | 0 |
| Sulfadiazine | Silver | 6.0 | 3.9 | 0 | 0 |
| Sulfadiazine | Zinc | 6.3 | 3.3 | 0 | 0 |
| Sulfadiazine | Cerium | 5.9 | 3.9 | 0 | 0 |

As can be seen from the data in Table III above, saline irrigation caused loss of antimicrobial agent in the norfloxacin-treated grafts, irrespective of whether the norfloxacin was bonded with, or without the metal. However, the metal-norfloxacin treated graft specimens retained a higher level of norfloxacin. While the various metals bound different amounts of norfloxacin initially, approximately identical amounts of norfloxacin were retained after saline irrigation.

Thus it appears that the metals induce both a stable and a labile binding of the norfloxacin. This differential binding pattern is desirable, since the metal norfloxacin complex, which dissociates rapidly, can provide an increased local concentration, while the tightly bound part may permit a steady, prolonged drug release at the graft site.

With respect to the other antimicrobial agents tested, silver-treated specimens retained a higher amount of antimicrobial agent upon saline irrigation than specimens treated without the metal, and indeed, retained the highest concentration of antimicrobial agent among the various metals. It appears that the use of other metals, such as zinc and cerium, may increase the uptake of antimicrobial agent into the polymeric material (PTFE) as shown in Tables II and III, but does not increase the retention of antimicrobial agent in the presence of normal saline. A possible explanation for this may be that the metal-antimicrobial agent complexes of zinc and cerium are more soluble in body fluids than is the silver complex.

(D) In regard to Table IV below, long-term stability of the treated PTFE vascular graft samples under in vivo conditions, where the graft is constantly exposed to circulating blood, was simulated by soaking a 1 cm segment of each of the various treated graft samples in 5 ml of human blood, which was agitated in a 37° C. water-bath shaker over a period of 10 days. The blood was changed daily. The antibacterial activity of the graft samples, at various time intervals, was tested by incubating the samples in nutrient broth culture containing $10^4$ Staph. aureus organisms for 24-48 hours. Aliquots of the nutrient broth culture were spread on blood agar plates, and a colony count was taken after 24 hours of incubation.

incorporaation therein from an organic solvent as described hereinabove in Example 5, with the aid of a TDMAC coating, and with the aid of an albumin coating.

Five grafts of each type were implanted in the canine infrarenal aorta and retrieved 20 minutes after declamping and 10 minutes after graft pore bleeding had ceased. The fraction of antimicrobial agent remaining 30 in the graft (1 cm segment) was determined by standard radiotracer techniques. Antibacterial activity was determined, in the same fashion as in the prior experiments, using a 1:1 proportional mixture of nutrient broth and blood containing $10^7$ Staph. aureus organisms. The results are shown below in Table V.

TABLE V

| | INITIAL | | POST RETRIEVAL | | |
|---|---|---|---|---|---|
| Graft | Drug Concentration ($\mu$ mole/cm) | Antibacterial Activity (Colony Count) | Drug Concentration ($\mu$ mole/cm) | % Retention | Antibacterial Activity (Colony Count) |
| AgNF - Aqueous Solvent | 5.8 | 0 | 0.51 | 9 | $4 \times 10^2$ |
| AgNF - TDMAC Coating | 13.1 | 0 | 3.7 | 28 | 5 |
| AgNF - Albumin Coating | 6.1 | 0 | 3.4 | 56 | 0 |
| AgNF - Organic Solvent | 10.6 | 0 | 5.0 | 47 | 0 |

These results in Table V above show that silver norfloxacin has a high degree of retention by uncoated Dacron polyester graft when the organic solvent technique of the present invention is applied. Moreover, the treated grafts were able to suppress bacterial growth even in canine blood circulation. While the initial concentration of the antimicrobial agent in the Dacron polyester graft samples bound by the novel organic solvent technique herein described was not quite as high as that bound with TDMAC coating technique, nevertheless the antibacterial activity of the graft was still retained.

(F) A further in vivo test was performed to show the long-term stability and antibacterial activity of treated Dacron polyester vascular graft specimens retrieved one week after implantation in dogs.

1 cm segments of Dacron polyester vascular grafts were implanted in the abdominal aorta of three dogs and challenged with $0.5 \times 10^7$ Staph. aureus. After one week, the grafts were retrieved and the number of bacteria in the grafts was determined as hereinabove.

TABLE IV

| | Antibacterial Activity (Colony Count) Days Post Exposure | | | | | | |
|---|---|---|---|---|---|---|---|
| Graft Bonded With: | 0 | 1 | 3 | 5 | 7 | 8 | 10 |
| None | $2 \times 10^8$ | | | | | | |
| Norfloxacin | 0 | 0 | $5 \times 10^4$ | $2 \times 10^4$ | $2 \times 10^6$ | $2 \times 10^6$ | $2 \times 10^8$ |
| Norfloxacin + Silver | 0 | 0 | $1 \times 10^2$ | $1 \times 10^2$ | 0 | $2 \times 10^3$ | $2 \times 10^3$ |
| Norfloxacin + Zinc | 0 | 0 | $5 \times 10^2$ | 0 | 0 | 0 | $6 \times 10^2$ |
| Norfloxacin + Cerium | 0 | 0 | $3 \times 10^3$ | $1 \times 10^3$ | $5 \times 10^2$ | 0 | $4 \times 10^2$ |
| Oxacillin | 0 | 0 | $2 \times 10^5$ | $2 \times 10^7$ | | | |
| Oxacillin + Silver | 0 | 0 | $2 \times 10^3$ | $2 \times 10^5$ | | | |
| Oxacillin + Zinc | 0 | 0 | $2 \times 10^3$ | $2 \times 10^5$ | | | |
| Oxacillin + Cerium | 0 | 0 | $1 \times 10^3$ | $2 \times 10^5$ | | | |

The results in Table IV above indicate that metal-mediated bonding is more effective in prolonging the anti-bacterial activity of the treated graft specimens.

(E) An in vivo test was performed to show the antimicrobial agent retention and antibacterial activity of Dacron polyester vascular graft specimens retrieved after implantation in dogs. Radioactive silver norfloxacin ($^{110}$AgNF) was bound to segments of Dacron grafts by incorporation therein from an aqueous solvent, by The results are shown below in Table VI wherein the control graft did not contain an antimicrobial agent and the oxacillin-treated and silver norfloxacin-treated grafts were prepared in accordance with the bonding procedure of Example 5.

TABLE VI

| Type of Graft | No. of Bacteria in Graft after Retrieval | | |
|---|---|---|---|
| | Dog 1 | Dog 2 | Dog 3 |
| Control | 100,000 | 1,000,000 | 10,000 |
| Oxacillin | 60 | 62 | 84 |
| Silver Norfloxacin | 100 | 320 | 220 |

The data in Table VI above show that the treated grafts, in contrast with the control grafts, exhibited low bacterial growth when tested after a week of in vivo canine blood circulation.

(G) Additional in vivo experiments were run to determine the long-term stability and antibacterial efficacy of PTFE vascular grafts bonded with a variety of antimicrobial agents in rat muscle pouch.

Sprague-Dawley rats that weighed 220–250 gm were housed in individual cages. At operation a 2 cm incision was made in the medial aspect of the thigh and a pouch was created by blunt dissection in the abductor muscle. Six segments (2 cm length) of PTFE graft, one in each group were then placed in the muscular pouch and infected with 0.1 ml of Staph. aureus culture containing $10^5$ bacteria After one week, the grafts were removed and bacterial counts were determined as hereinabove. The results are shown in Table VIIA below wherein the control graft did not contain an antimicrobial agent; the oxacillin, norfloxacin, pefloxacin and tobramycin grafts were prepared by the bonding procedure of Example 2; and the silver oxacillin, silver norfloxacin and silver pefloxacin grafts were prepared by the bonding procedure of Example 1.

TABLE VIIA

| Group | No. of Bacteria Colonies | |
|---|---|---|
| | Graft | Graft-Bed |
| Control Graft | 100,000 | 100,000 |
| Oxacillin Graft | 10 | 20 |
| Silver Oxacillin Graft | 15 | 30 |
| Norfloxacin Graft | 20 | 50 |
| Silver Norfloxacin Graft | 10 | 25 |
| Pefloxacin Graft | 0 | 0 |
| Silver Pefloxacin Graft | 0 | 0 |
| Tobramycin Graft | 0 | 0 |

The data in Table VIIA above show that the grafts treated with a variety of antimicrobial agents and silver salts thereof, unlike the control graft, were able to suppress bacterial growth in this in vivo rat experiment.

The data in Table VIIB below show the drug retention in PTFE vascular grafts retrieved from an uninfected rat muscle pouch after 1–5 days of implantation. The oxacillin and pefloxacin grafts were prepared by the bonding procedure of Example 2, while the silver oxacillin and silver pefloxacin grafts were prepared by the bonding procedure of Example 1.

TABLE VIIB

Drug Retention Expressed as Antibacterial Activity (No. of colonies in culture and zones of inhibition)

| Drug in Graft | Days of Implantation | | | | |
|---|---|---|---|---|---|
| | 1 | 2 | 3 | 4 | 5 |
| Oxacillin | 0 (37) | 0 (35) | 0 (30) | $10^4$ (23) | $10^4$ (0) |
| Silver Oxacillin | 0 (37) | 0 (35) | 0 (28) | $10^1$ (33) | $10^2$ (17) |
| Pefloxacin | 0 (38) | 0 (35) | 0 (33) | $10^1$ (33) | $10^4$ (14) |
| Silver Pefloxacin | 0 (38) | 0 (35) | 0 (34) | 0 (35) | $2 \times 10^2$ (30) |

TABLE VIIB-continued

Drug Retention Expressed as Antibacterial Activity (No. of colonies in culture and zones of inhibition)

| Drug in Graft | Days of Implantation | | | | |
|---|---|---|---|---|---|
| | 1 | 2 | 3 | 4 | 5 |
| Pefloxacin | | | | | |

Figures in ( ) are zones of inhibition

In Table VIIB above, the figures in parentheses are zones of inhibition in mm. After various intervals of implantation in the rat muscle pouch, the grafts were retrieved and the antibacterial activity tested against $10^7$ Staph. aureus grown in 5 ml blood. The zone of inhibition was measured against $10^4$ Staph. aureus spread on blood agar plate.

(H) Silver norfloxacin (AgNF) and silver perfloxacin (AgPF) were bonded to two types of Foley catheters by the method of the present invention.

8 mm pieces of catheter were soaked for 3 minutes in 30 mM pefloxacin or norfloxacin solution in a 1:25 by volume mixture of acetic acid and chloroform. After removal, they were air dried for 10 minutes and soaked in 25mM silver nitrate solution in ethanol for 5 minutes. After air drying, the catheters were resoaked in the original pefloxacin or norfloxacin solution for 3 minutes. The pieces were air dried and tested for antibacterial activity as hereinabove. 2 cm pieces were suspended in urine containing $10^4$ bacteria The results are shown in Table VIII below.

TABLE VIII

| Silicone Elastomer Catheter | | | Hydrophilic Latex Catheter | | |
|---|---|---|---|---|---|
| Drug in 2 cm Piece μ mole (mg) | Colony Counts in Culture | | Drug in 2 cm Piece μ mole (mg) | Colony Counts in Culture | |
| | Staph. aureus | Ps. aer. | | Staph. aureus | Ps. aer. |
| AgNF 0.8 (0.22) | 0 | 0 | AgNF 0.9 (0.28) | 0 | 0 |
| AgPF 1.0 (0.3) | 0 | 0 | AgPF 1.0 (0.45) | 0 | 0 |
| Untreated Control | $10^4$ | $10^4$ | Untreated Control | $10^4$ | $10^4$ |

The data in Table VIII above show that the method of the present invention can be used satisfactorily in imparting infection resistance to catheters made of different polymeric materials.

(I) Silver sulfadiazine was incorporated into sutures (Ethicon-Black braided silk and 0 Dexon Polyglycolic) using the following procedure.

2 ml of 300 mM sodium sulfadiazine were mixed with 6 ml ethanol and 2 ml chloroform (final conc. of sodium sulfadiazine 60 μ mole/ml). 60 cm pieces of the suture were soaked in the above solution for 30 minutes, removed, blotted dry and soaked in an ethanolic solution of silver nitrate (50 μ mole/ml) for 5 minutes. After removing and blotting off excess fluid, the suture was resoaked in the original sodium sulfadiazine solution for 30 minutes. The suture was dried and tested for drug content and antibacterial activity against $10^4$ organism in 5 ml broth. The results are shown in Table IX below.

TABLE IX

| Suture | Concentration of Drug μ mole (mg) | Antibacterial Activity | |
|---|---|---|---|
| | | Ps. aeruginosa | Staph. aureus |
| Silk (25 cm) | 1.1 (0.4) | Bacteriocidal | Bacteriocidal |

TABLE IX-continued

| Suture | Concentration of Drug μ mole (mg) | Antibacterial Activity | |
|---|---|---|---|
| | | Ps. aeruginosa | Staph. aureus |
| Polyglycolic (25 cm) | 1.7 (0.6) | Bacteriocidal | Bacteriocidal |

The data in Table IX above further show that the method of the present invention can also be used satisfactorily in imparting infection-resistance to sutures made of different polymeric materials.

(J) Table X below shows the in vivo antimicrobial efficacy of Dacron polyester grafts bonded with various antibiotics and prepared by the modified procedure of Example 6. These Dacron polyester grafts seem to bind more antibiotic than the PTFE graft (See Table I) and also exhibit high antibacterial activity.

TABLE X

| Grafts Bonded with | Drug Concentration (μ mole/2 cm graft) | Antibacterial Activity in Blood Culture (Colony Count) |
|---|---|---|
| None (Control) | 0 | $10^7$ |
| Norfloxacin | 8.0 | 0 |
| Silver Norfloxacin | 12.0 | 0 |
| Oxacillin | 10.0 | 0 |
| Silver Oxacillin | 15.0 | 0 |

In Table X above, a 1 cm segment of the Dacron polyester graft was soaked in 5 ml blood containing *Staph. aureus* ($10^7$ organisms) and inoculated at 37° C. for 24 to 48 hours. Bacterial growth in the blood culture was measured by plating 0.2 ml aliquot of culture on blood agar plate.

What is claimed is:

1. A method of preparing an infection-resistant polymeric material for use on or within a human or animal body which comprises the following sequence of steps:

(a) soaking a polymeric material with a solution of an antimicrobial agent dissolved in an organic solvent therefor, (b) soaking the polymeric material with an organic solvent for a metal salt, (c) resoaking the polymeric material with the solution of the antimicrobial agent dissolved in the organic solvent therefor, and (d) drying the polymeric material after each soaking step.

2. A method according to claim 1 wherein in step (b) said organic solvent contains a metal salt dissolved therein.

3. A method according to claim 2 wherein the metal of the metal salt is selected from the group consisting of silver, zinc and cerium.

4. A method according to claim 3 wherein said metal is silver.

5. A method according to claim 1 or 4 wherein said antimicrobial agent is norfloxacin.

6. A method according to claim 1 or 4 wherein said antimicrobial agent is oxacillin.

7. A method according to claim 1 or 4 wherein said antimicrobial agent is nafcillin.

8. A method according to claim 1 or 4 wherein said antimicrobial agent is sulfadiazine.

9. A method according to claim 1 or 4 wherein said antimicrobial agent is pefloxacin.

10. A method according to claim 1 or 4 wherein said antimicrobial agent is tobramycin.

11. A method according to claim 1 or 4 wherein said polymeric material is polytetrafluoroethylene.

12. A method according to claim 1 or 4 wherein said polymeric material is a polyester.

13. A method according to claim 1 or 4 wherein said polymeric material is a silicone elastomer.

14. A method according to claim 1 or 4 wherein said polymeric material is silk.

15. A method according to claim 1 or 4 wherein the polymeric material is a polyester and the polymeric material is resoaked with the solution of the antimicrobial agent dissolved in the organic solvent therefor which contains a small amount of polylactic acid.

* * * * *

UNITED STATES PATENT AND TRADEMARK OFFICE
CERTIFICATE OF CORRECTION

PATENT NO. : 4,612,337

DATED : September 16, 1986

INVENTOR(S) : Charles L. Fox, Jr., et al

It is certified that error appears in the above-identified patent and that said Letters Patent is hereby corrected as shown below:

Col. 1, line 27, after "application" delete "for".

Col. 10, line 8, after "remaining" delete "30"; line 13, "10 $^7$" should read -- $10^7$ --; line 44, "10 $^7$" should read -- $10^7$ --. Col. 12, line 18, "perfloxacin" should read -- pefloxacin --.

Signed and Sealed this

Twenty-seventh Day of January, 1987

Attest:

DONALD J. QUIGG

Attesting Officer     Commissioner of Patents and Trademarks